United States Patent [19]

Jolley et al.

[11] Patent Number: 5,302,305

[45] Date of Patent: Apr. 12, 1994

[54] CARBOXYLIC ESTERS, LIQUID COMPOSITIONS CONTAINING SAID CARBOXYLIC ESTERS AND METHODS OF LUBRICATING METAL PARTS

[75] Inventors: Scott T. Jolley, Mentor; Richard M. Lange, Euclid, both of Ohio

[73] Assignee: The Lubrizol Corporation, Wickliffe, Ohio

[21] Appl. No.: 310,146

[22] Filed: Feb. 9, 1989

[51] Int. Cl.$^5$ .................................... C10M 137/12
[52] U.S. Cl. ............................ 252/32.005; 558/180
[58] Field of Search ................... 252/32.5, 56 R; 558/180

[56] References Cited

U.S. PATENT DOCUMENTS

| | | | |
|---|---|---|---|
| 2,989,562 | 6/1981 | Swern | 558/160 |
| 3,012,054 | 12/1961 | Moss | 558/160 |
| 3,763,287 | 10/1973 | Chiddix et al. | 558/179 |
| 3,772,412 | 11/1973 | Quimby et al. | 558/179 |
| 4,101,432 | 7/1978 | Okorodudu | 558/180 |
| 4,248,726 | 2/1981 | Uchinuma et al. | 252/52 A |
| 4,267,064 | 5/1981 | Sasaki et al. | 252/52 A |
| 4,332,746 | 6/1982 | Thamm | 558/160 |
| 4,428,854 | 1/1984 | Enjo et al. | 252/69 |
| 4,431,557 | 2/1984 | Shimizu et al. | 252/52 A |
| 4,454,052 | 6/1984 | Shoji et al. | 252/68 |
| 4,539,355 | 9/1985 | Takahashi et al. | 558/179 |
| 4,559,154 | 12/1985 | Powell | 252/69 |
| 4,755,316 | 7/1988 | Magid et al. | 252/68 |
| 4,766,015 | 8/1988 | Nikoloff et al. | 252/49.8 |

FOREIGN PATENT DOCUMENTS 60132A 9/1982 European Pat. Off. .

OTHER PUBLICATIONS

G. Borisov et al., "Synthesis of Phosphorylated Esters and Oligoesters, Prepared from Unsaturated Acids and Glycols, and Their Use as Flame Retardants for Rigid Polyurethane Foams", *European Polymer Journal*, vol. 24, No. 8, 1988, pp. 741–745.

*Methoden der Organische Chemie*, vol. 121, pp. 463–475, Houben Weyle, date not available.

*Organic Reactions*, vol. XIII, pp. 218–223 and 354–359, date not available.

*Tetrahedron*, 1966, vol. 22, pp. 2561–2573, date not available.

*Primary Examiner*—Jacqueline V. Howard
*Attorney, Agent, or Firm*—Frederick D. Hunter; Forrest L. Collins; James A. Cairns

[57] ABSTRACT

Phosphorus-containing compositions and carboxylic ester compositions are described. The esters are useful as synthetic lubes and as lubricants in liquid compositions containing fluorine-containing hydrocarbons. A liquid composition also is described comprising (A) a major amount of a fluorine containing hydrocarbon containing one or two carbon atoms, and (B) a minor amount of a soluble organic lubricant comprising at least one carboxylic ester characterized by the formulae

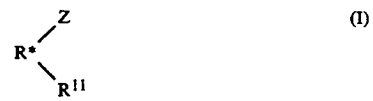

(I)

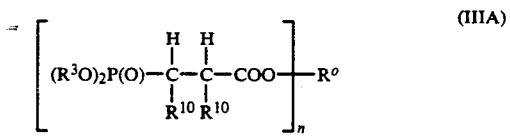

(IIIA)

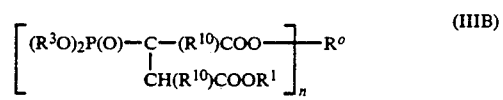

(IIIB)

and

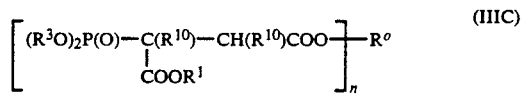

(IIIC)

wherein
R* is a hydrocarbylene group or a hydrocarbylene group substituted with a —P(O)(OR$^3$)$_2$ group;
Z is —COOR$^1$, —C(O)NR$^4$R$^5$, —C(O)(OR$^6$)yN(R$^4$)-

(Abstract continued on next page.)

ABSTRACT $C(O)R^7$, $C(O)(OR^6)yOC(O)R^7$, —CN, —CHO, or —$C(O)R^7$;

$R^o$ is an alkylene group;

$R^1$ is a hydrocarbyl group or a hydrocarbyloxy hydrocarbyl group and $R^1$ may be the same as $R^3$;

$R^3$ is independently a hydrocarbyl group;

$R^4$ and $R^5$ are each independently H or hydrocarbyl groups;

$R^6$ is a hydrocarbylene group;

$R^7$ is a hydrocarbyl group;

y is an integer from 1 to about 20;

$R^{10}$ is independently H or a hydrocarbyl group;

$R^{11}$ is H, or —$COOR^1$; and n is an integer from 2 to about 6, provided that in Formula I, at least one of Z or $R^{11}$ is a —$COOR^1$ group, and when both Z and $R^{11}$ are —$COOR^1$, $R^*$ is a hydrocarbylene group substituted with a —$P(O)(OR^3)_2$ group. The liquid compositions of the invention are useful particularly as refrigeration liquids in refrigerators and air-conditioners including auto, home and industrial air-conditioners.

7 Claims, No Drawings

CARBOXYLIC ESTERS, LIQUID COMPOSITIONS CONTAINING SAID CARBOXYLIC ESTERS AND METHODS OF LUBRICATING METAL PARTS

FIELD OF THE INVENTION

This invention relates to carboxylic esters and more particularly to phosphorus-containing carboxylic esters and their use as synthetic lubricants and as lubricants in liquid compositions containing liquid fluorine-containing hydrocarbons. More particularly, the invention relates to synthetic lubricants and to liquid compositions useful as refrigeration liquids.

BACKGROUND OF THE INVENTION

Reactions of trialkyl phosphites with various alpha,-beta-unsaturated acids, esters, ketones, aldehydes, amides and nitriles in protonating solvents has been described in literature. For example, see *Tetrahedron*, 1966, Vol. 22, pages 2561-2573. Reactions of dialkyl phosphites with activated olefins such as those mentioned above by a free radical mechanism also have been described in the literature such as, for example, in *Methoden Der Organische Chemie*, Vol. 12/1, pages 463-475, Houben-Weyl. Phosphorus-containing compositions prepared by the above processes are useful in a variety of applications. For example, they are useful as fire-retardant additives.

The present invention relates to the use of certain types of phosphorus-containing carboxylic acid esters as synthetic lubricants and as lubricants useful in compositions comprising a major amount of a fluorine-containing hydrocarbon of the type generally used in refrigeration systems.

Chlorofluorocarbons, generally referred to in the industry as CFCS, have been widely used as propellants in aerosols, although use in aerosols has been diminishing in recent years because of demands of environmentalists for the reduction if not a complete ban on the use of CFCs because of the detrimental effect of CFCs on the atmosphere's ozone layer. CFCs also have been used because of their unique combination of properties as refrigerants, foam-blowing agents, and specialty solvents within the electronics and aerospace industries. Examples of CFCs which have been utilized for these purposes include CFC-11 which is chlorotrifluoromethane, CFC-12 which is dichlorodifluoromethane, and CFC-113 which is 1,2,2-trifluoro-1,1,2-trichloroethane.

Since 1976, when the aerosol industry began to feel the pressure to reduce if not eliminate the use of CFCs, the aerosol industry has progressively moved toward the substitution of hydrocarbon propellants for CFC propellants. The hydrocarbons, such as butane, are readily available and inexpensive, and the quality of the final product generally has been unaffected by the substitution of propellants. However, the problem of finding a safe replacement of CFC refrigerants and foam-blowing agents has been more difficult to solve. Several replacement candidates have been suggested as alternatives to the fully halogenated hydrocarbons, and these include halogenated hydrocarbons containing at least some hydrogen atoms such as HCFC-22 which is difluorochloromethane, HCFC-123 which is 1,1-dichloro-2,2,2-trifluoroethane, HFC-134a which is 1,1,1,2-tetrafluoroethane and HCFC-141b which is 1,1-dichloro-1-fluoroethane.

The ozone depletion potential of these proposed substitutes is significantly less than the ozone depletion potential of the previously used CFCS. The ozone depletion potential is a relative measure of the capability of the material to destroy the ozone layer in the atmosphere. It is a combination of the percentage by weight of chlorine (the atom that attacks the ozone molecule) and the lifetime in the atmosphere. HCFC-22 and HFC-134a generally are recommended as being candidates in refrigerant applications, and HFC-134a is particularly attractive because its ozone depletion potential has been reported as being zero.

In order for any of the replacement materials to be useful as refrigerants, the materials must be compatible with the lubricant utilized in the compressor. The presently used refrigerants such as CFC-12 are readily compatible with mineral lubricating oils which are utilized as the lubricant in air-conditioner compressors. The above-described refrigerant candidates, however, have different solubility characteristics than the refrigerants presently in use. For example, mineral lubricating oil is incompatible (i.e., insoluble) with HFC-134a. Such incompatibility results in unacceptable compressor life in compression-type refrigeration equipment including refrigerators and air-conditioners including auto, home and industrial air-conditioners. The problem is particularly evident in automotive air-conditioning systems since the compressors are not separately lubricated, and a mixture of refrigerant and lubricant circulates throughout the entire system.

In order to perform as a satisfactory refrigeration liquid, the mixture of refrigerant and lubricant must be compatible and stable over a wide temperature range such as from about 0° C. and above 80° C. It is generally desirable for the lubricants to be soluble in the refrigerant at concentrations of about 5 to 15% over a temperature range of from −40° C. to 80° C. These temperatures generally correspond to the working temperatures of an automobile air-conditioning compressor. In addition to thermal stability, the refrigeration liquids must have acceptable viscosity characteristics which are retained even at high temperatures, and the refrigeration liquid should not have a detrimental effect on materials used as seals in the compressors.

Compositions comprising a tetrafluoroethane and polyoxyalkylene glycols are discussed in U.S. Pat. No. 4,755,316. The compositions are useful in refrigeration systems. Refrigeration oils are described in U.S. Pat. Nos. 4,248,726 and 4,267,064 which comprise mixtures of a polyglycol and 0.1 to 10% of glycidyl ether type epoxy compounds, or epoxidized fatty acid monoesters, and optionally, epoxidized vegetable oil. The lubricating oils are reported to be useful in refrigerators using a halogen-containing refrigerant such as Freons 11, 12, 13, 22, 113, 114, 500 and 502 (available from DuPont), and in particular with Freon 12 or 22.

U.S. Pat. No. 4,431,557 describes fluid compositions comprised of a fluoro- and chloro-containing refrigerant, a hydrocarbon oil, and an alkylene oxide additive compound which improves the thermal resistance of the oil in the presence of the refrigerant. Examples of hydrocarbon oils include mineral oil, alkyl benzene oil, dibasic acid ester oil, polyglycols, etc. The composition may contain other additives including load-carrying additives such as phosphorus acid esters, phosphoric acid esters, etc. Examples of fluorocarbon refrigerants include R-11, R-12, R-113, R-114, R-500, etc.

U.S. Pat. No. 4,428,854 describes absorption refrigerant compositions for use in refrigeration systems comprising 1,1,1,2-tetrafluoroethane and an organic solvent capable of dissolving the ethane. Among the solvents disclosed are organic amides, acetonitrile, N-methyl pyrroles, N-methyl pyrrolidine, N-methyl-2-pyrrolidone, nitromethane, various dioxane derivatives, glycol ethers, butyl formate, butyl acetate, diethyl oxalate, diethyl malonate, acetone, methyl ethyl ketone, other ketones and aldehydes, triethyl phosphoric triamide, triethylene phosphate, triethyl phosphate, etc.

Stabilized absorption compositions comprising (a) a halogenated hydrocarbon refrigerant, (b) a liquid absorbent of a polyethylene glycol methyl ether, and (c) at least one stabilizer are described in U.S. Pat. No. 4,454,052. Examples of stabilizers include phosphate esters, epoxy compounds, and organotin compounds. The polyethylene glycol methyl ether-type compounds are of the general formula $$CH_3-O-(CH_2H_4O)_nR$$

wherein n is an integer of 1 to 6, and R is H, $CH_3-$ or $CH_3CO-$. A variety of halogenated hydrocarbons are described including 1,1,-difluoromethane, 1,1,1,2-tetrafluoroethane, etc.

U.S. Pat. No. 4,559,154 relates to absorption heat pumps utilizing as working fluid, a saturated fluorohydrocarbon or fluorohydrocarbon ether having from 3 to 5 carbon atoms. Solvents reported to be useful with such fluorohydrocarbons include ethers such as tetraglyme, amides which can be lactams such as the N-alkyl pyrrolidones, sulfonamides and ureas including cyclic ureas.

SUMMARY OF THE INVENTION

Phosphorus-containing compositions and carboxylic ester compositions are described. The esters are useful as synthetic lubes and as lubricants in liquid compositions containing fluorine-containing hydrocarbons. A liquid composition also is described comprising (A) a major amount of a fluorine containing hydrocarbon containing one or two carbon atoms, and (B) a minor amount of a soluble organic lubricant comprising at least one carboxylic ester characterized by the formulae

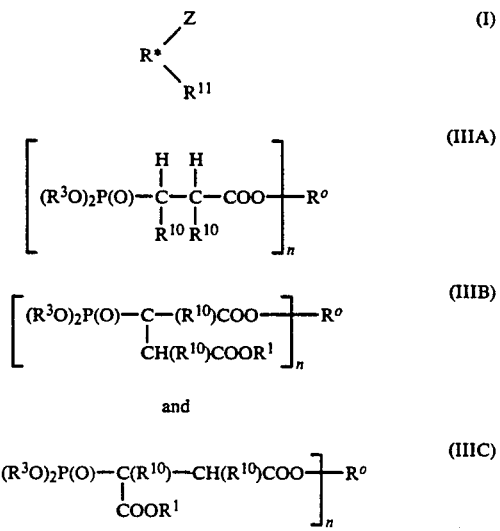

wherein $R^*$ is a hydrocarbylene group or a hydrocarbylene group substituted with a $-P(O)(OR^3)_2$ group;

Z is $-COOR^1$, $-C(O)NR^4R^5$, $-C(O)(OR^6)_yN(R^4)-C(O)R^7$, $-C(O)(OR^6)_yOC(O)R^7$, $-CN$, $-CHO$, or $-C(O)R^7$;

$R^o$ is an alkylene group;

$R^1$ is a hydrocarbyl group or a hydrocarbyloxy hydrocarbyl group and $R^1$ may be the same as $R^3$;

$R^3$ is independently a hydrocarbyl group;

$R^4$ and $R^5$ are each independently H or hydrocarbyl groups;

$R^6$ is a hydrocarbylene group;

$R^7$ is a hydrocarbyl group;

y is an integer from 1 to about 20;

$R^{10}$ is independently H or a hydrocarbyl group;

$R^{11}$ is H, or $-COOR^1$; and n is an integer from 2 to about 6, provided that in Formula I, at least one of Z or $R^{11}$ is a $-COOR^1$ group, and when both Z and $R^{11}$ are $-COOR^1$, $R^*$ is a hydrocarbylene group substituted with a $-P(O)(OR^3)_2$ group. The liquid compositions of the invention are useful particularly as refrigeration liquids in refrigerators and air-conditioners including auto, home and industrial air-conditioners.

DESCRIPTION OF THE PREFERRED EMBODIMENTS

Throughout this specification and claims, all parts and percentages are by weight, temperatures are in degrees Celsius, and pressures are at or near atmospheric unless otherwise clearly indicated.

As used in this specification and in the appended claims, the terms "hydrocarbyl" and "hydrocarbylene" denote a group having a carbon atom directly attached to the polar group and having a hydrocarbon or predominantly hydrocarbon character within the context of this invention. Such groups include the following:

(1) Hydrocarbon groups; that is, aliphatic, (e.g., alkyl or alkenyl), alicyclic (e.g., cycloalkyl or cycloalkenyl), and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, etc.

(2) Substituted hydrocarbon groups; that is, groups containing non-hydrocarbon substituents which, in the context of this invention, do not alter the predominantly hydrocarbon character of the group. Those skilled in the art will be aware of suitable substituents. Examples include halo, hydroxy, alkoxy, etc.

(3) Hetero groups; that is, groups which, while predominantly hydrocarbon in character within the context of this invention, contain atoms other than carbon in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl group.

Terms such as "alkyl", "alkylene", etc. have meanings analogous to the above with respect to hydrocarbyl and hydrocarbylene.

The term "hydrocarbon-based" also has the same meaning and can be used interchangeably with the term hydrocarbyl when referring to molecular groups having a carbon atom attached directly to the polar group.

The term "lower" as used herein in conjunction with terms such as hydrocarbyl, alkyl, alkenyl, alkoxy, and the like, is intended to describe such groups which contain a total of up to 7 carbon atoms.

The Liquid Compositions of the Invention

In one aspect, the present invention relates to phosphorus-containing carboxylic esters which are useful as synthetic lubricants and as lubricants in the liquid compositions of the present invention. The invention also relates to carboxylic esters which do not contain phosphorus and which are useful as lubricants in the liquid compositions of the present invention. The liquid compositions of the present invention comprise a major amount of a fluorine-containing hydrocarbon.

(A) Fluorine-Containing Hydrocarbon

The fluorine-containing hydrocarbon present in the liquid compositions contain at least one C—H bond as well as C—F bonds. In addition to these two essential types of bonds, the hydrocarbon also may contain other carbon-halogen bonds such as C—Cl bonds. Because the liquid compositions of the present invention are primarily intended for use as refrigerants, the fluorine-containing hydrocarbon preferably contains one or two carbon atoms, and more preferably two carbon atoms.

As noted above, the fluorine-containing hydrocarbons useful in the liquid compositions of the present invention may contain other halogens such as chlorine. However, in one preferred embodiment, the hydrocarbon contains only carbon, hydrogen and fluorine. These compounds containing only carbon, hydrogen and fluorine are referred to herein as fluorohydrocarbons. The hydrocarbons containing chlorine as well as fluorine and hydrogen are referred to as chlorofluorohydrocarbons. The fluorine-containing hydrocarbons useful in the composition of the present invention are to be distinguished from the fully halogenated hydrocarbons which have been and are being used as propellants, refrigerants and blowing agents such as CFC-11, CFC-12 and CFC-113 which have been described in the background.

Specific examples of the fluorine-containing hydrocarbons useful in the liquid compositions of the present invention, and their reported ozone depletion potentials are shown in the following Table I.

TABLE I

| Compound Designation | Formula | ODP* |
|---|---|---|
| HCFC-22 | CHClF$_2$ | 0.05 |
| HCFC-123 | CHCl$_2$CF$_3$ | <0.05 |
| HCFC-141b | CH$_3$CCl$_2$F | <0.05 |
| HFC-134a | CH$_2$FCF$_3$ | 0 |

*Ozone depletion potential as reported in Process Engineering, pp. 33–34, July, 1988.

Examples of other fluorine-containing hydrocarbons which may be useful in the liquid compositions of the present invention include trifluoromethane, 1,1,1-trifluoroethane, 1,1-difluoroethane, and 1,1,2,2-tetrafluoroethane.

In general, fluorine-containing hydrocarbons which are useful as refrigerants are fluoromethanes and fluoroethanes boiling at a relatively low temperature at atmospheric pressure, e.g., below 30° C. The useful fluorocarbon refrigerants serve to transfer heat in a refrigeration system by evaporating and absorbing heat at a low temperature and pressure, e.g., at ambient temperature and atmospheric pressure, and by releasing heat on condensing at a higher temperature and pressure.

The liquid compositions of the present invention contain a major amount of the fluorine-containing hydrocarbon. more generally, the liquid compositions will comprise from about 50% to about 99% by weight of the fluorine-containing hydrocarbon. In another embodiment, the liquid compositions contain from about 70% to about 99% by weight of the fluorine-containing hydrocarbon.

(B) Soluble Organic Lubricant

In addition to the fluorine-containing hydrocarbon, the liquid compositions of the present invention contain a minor amount of a soluble organic lubricant comprising at least one carboxylic ester characterized by the following formulae

(I)

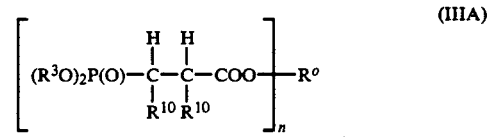
(IIIA)

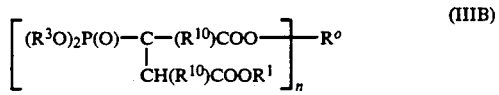
(IIIB)

and

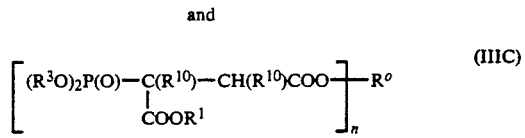
(IIIC)

wherein

R* is a hydrocarbylene group or a hydrocarbylene group substituted with a —P(O)(OR$^3$)$_2$ group;

Z is —COOR$^1$, —C(O)NR$^4$R$^5$, —C(O)(OR$^6$)yN(R$^4$)-C(O)R$^7$, —C(O)(OR$^6$)yOC(O)R$^7$, —CN, —CHO, or —C(O)R$^7$;

R$^o$ is an alkylene group;

R$^1$ is a hydrocarbyl group or a hydrocarbyloxy hydrocarbyl group and R$^1$ may be the same as R$^3$;

R$^3$ is independently a hydrocarbyl group;

R$^4$ and R$^5$ are each independently H or hydrocarbyl groups;

R$^6$ is a hydrocarbylene group;

R$^7$ is a hydrocarbyl group;

y is an integer from 1 to about 20;

R$^{10}$ is independently H or a hydrocarbyl group;

R$^{11}$ is H, or —COOR$^1$; and n is an integer from 2 to about 6, provided that in Formula I, at least one of Z or R$^{11}$ is a —COOR$^1$ group, and when both Z and R$^{11}$ are —COOR$^1$, R* is a hydrocarbylene group substituted with a —P(O)(OR$^3$)$_2$ group.

The organic lubricants characterized by the above formulae are preferably free of acetylenic and aromatic unsaturation. Compounds which contain such unsaturation generally are insoluble in the fluorine-containing hydrocarbons and in particular, in 1,1,1,2-tetrafluoroethane. The soluble lubricants of this invention also are preferably free of olefinic unsaturation except that some olefinic unsaturation may be present so long as the lubricant is soluble.

The liquid compositions of the present invention contain a minor amount of one or more of the above-described carboxylic ester lubricants (I) and (IIIA-C). More generally, the liquid compositions of the present invention will comprise from about 1 to about 49% by weight of the carboxylic ester lubricant. In a preferred embodiment, the liquid compositions contain from about 1 to about 30% by weight of the carboxylic ester lubricants.

In Formula I, the hydrocarbylene group R* may be a straight chain or a branched chain hydrocarbylene group, and the hydrocarbylene group may contain hetero atoms such as oxygen, sulfur or nitrogen in the hydrocarbylene chain. In another embodiment, R* is a hydrocarbylene group substituted with a $-P(O)(OR^3)_2$ group wherein each $R^3$ is independently a hydrocarbyl group. Generally, $R^3$ is a lower alkyl group, and more particularly, each $R^3$ is independently a methyl, ethyl or butyl group. The hydrocarbyl groups $R^1$, $R^4$, $R^5$, $R^7$ and $R^{10}$ may each independently contain from 1 to about 20 or more carbon atoms.

In Formula I, Z may be $-COOR^1$, $-C(O)NR^4R^5$, $-C(O)(OR^6)yN(R^4)C(O)R^7$, $-C(O)(OR^6)yOC(O)R^7$, $-CN$, $-CHO$ or $-C(O)R^7$ provided that at least one of Z or $R^{11}$ is a $-COOR^1$ group. Thus, $R^{11}$ may be H or $-COOR^1$ when Z is $-COOR^1$, but if Z is not $-COOR^1$, then $R^{11}$ must be $-COOR^1$. In one preferred embodiment, Z is $-COOR^1$, $-C(O)NR^4R^5$, or $-C(O)(OR^6)yNR^4C(O)R^7$. When both Z and $R^{11}$ are $-COOR^1$, one of the $R^1$ groups generally is $R^3$. Also, when both Z and $R^{11}$ are $-COOR^1$, R* is a hydrocarbylene group substituted with a $-P(O)(OR^3)_2$ group.

As noted above, $R^o$ is an alkylene group and $R^6$ is a hydrocarbylene group. Both of these groups may be straight-chain or branched-chain groups generally containing from 1 to 3 or 4 carbon atoms, and they may contain other substituents such as hydroxyl groups.

Carboxylic acids of the type represented by Formula I may be prepared by techniques well known to those in the art. In one method, trialkyl phosphites are reacted with activated olefins such as alpha,betaunsaturated carboxylic acids, esters, amides, nitriles, aldehydes, ketones, etc. The preparation of a variety of such phosphorus-containing esters described in *Tetrahedron*, 1966, Vol. 22, pages 2561-2573.

The reaction of a trialkyl phosphite with olefins activated with one or more carboxylic acid or ester groups are illustrated as in the following equations:

Monocarboxylic Acid

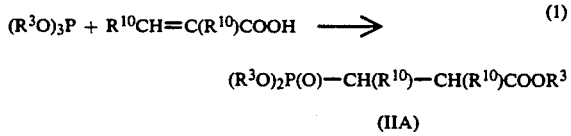

(IIA)

Equation 1 illustrates the addition of the phosphite moiety to the beta carbon in a conjugative manner which is believed to be the major product. The product may contain a small amount of material formed by addition of the phosphite moiety to the alpha carbon atom.

Dicarboxylic Acid

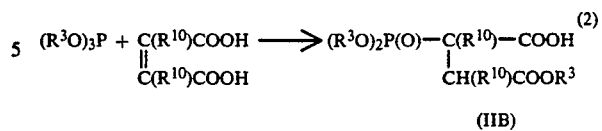

(IIB)

The product of Equation 2 may contain, in addition to IIB, some material like IIB but where the phosphite moiety is in the carbon atom alpha to the $COOR^3$ group. The major material in the product, however, should be IIB.

Dicarboxylic Acid Monoester

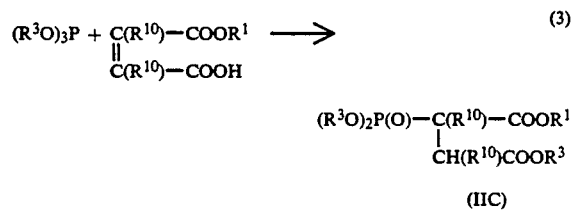

(IIC)

Another method for preparing the carboxylic esters of the present invention involves the reaction of a dialkyl phosphite with a carboxylic ester in the presence of a free radical-generating catalyst. The reaction is illustrated as follows:

Monocarboxylic Acid

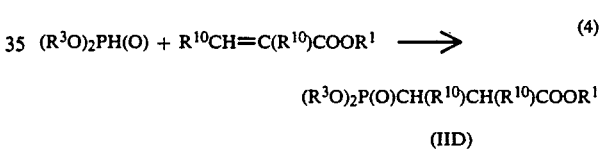

(IID)

The reaction product may also contain in addition to IID, some material obtained by the addition of the phosphite to the carbon atom alpha to the $COOR^1$ group.

Dicarboxylic Acid Ester

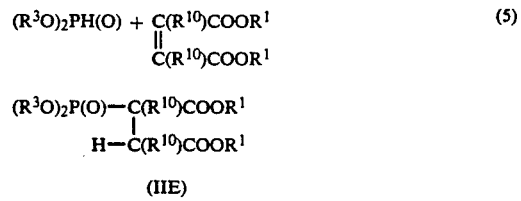

(IIE)

The phosphite group may add to either carbon atom. If the two $R^{10}$ groups are not the same or the two $R^1$ groups are different, the product may comprise a mixture of different isomers of IIE.

$R^{10}$ in the above formula may be H or a hydrocarbyl group.

The activated olefins which are reacted with dialkyl or tri-alkyl phosphites described above, in addition to being carboxylic acids or esters ($COOR^1$) may be olefins activated by the following groups: $-C(O)N-R^4R^5$ or $-C(O)(OR^6)yN(R^4)C(O)R^7$, $-C(O)-(OR^6)OC(O)R^7$, $-CN$, $-CHO$, or $-C(O)R^7$, wherein $R^1$, $R^4$, $R^5$, $R^6$, $R^7$ and y are as defined with respect to Formula I. The activated olefins may contain two or more of the activating groups such as two —COOR$^1$ groups (as described above) or a COOR$^1$ and any one of the other groups.

Thus, for example, the starting mono acid may be acrylic acid or substituted acrylic acids such as methacrylic acid, crotonic acid, 2-hexenoic acid, 4-methyl-2-pentenoic acid, etc. The corresponding methyl esters, ethyl esters, etc., may also be used. Examples of dicarboxylic acids include maleic acid and substituted maleic acids. The corresponding mono- and diesters can also be utilized as described above.

Carboxylic esters utilized in the liquid composition of the present invention also may be characterized by the formula

 (II)

wherein each

R is independently R$^{10}$ or (R$^3$O)$_2$P(O) provided that one R is (R$_3$O)$_2$P(O) and the other is R$^{10}$;
R$^{10}$ is independently H or a hydrocarbyl group;
R$^{11}$ is H or —COOR$^1$;
R$^1$ is H, a hydrocarbyl group or a hydrocarbyloxy group provided that at least one R$^1$ is not H;
Z is —COOR$^1$, —C(O)NR$^4$R$^5$, —C(O)(OR$^6$)yN—(R$^4$)C(O)R$^7$, —C(O)(OR$^6$)yOC(O)R$^7$, —CN, —CHO or —C(O)R$^7$;
R$^3$ is independently a hydrocarbyl group;
R$^4$ and R$^5$ are each independently H or hydrocarbyl groups;
R$^6$ is a hydrocarbylene group;
R$^7$ is a hydrocarbyl group; and
y is an integer from 1 to about 20.

When Z is COOR$^1$ and R$^{11}$ is H, the ester of Formula II is derived from alpha, beta-unsaturated monocarboxylic acids or esters such as acrylic acid and derivatives thereof, and when both Z and R$^{11}$ are COOR$^1$, the esters are derived from dicarboxylic acids or esters such as maleic acid, fumaric acid and derivatives thereof.

In another embodiment, the carboxylic ester utilized in the liquid compositions of the present invention may be represented by the following formula

 (IIF)

wherein R is H, a hydrocarbyl group, or —P(O)(OR$^3$)$_2$ and R$^2$ is —OR$^1$, —NR$^4$R$^5$, —(OR$^6$)yN(R$^4$)C(O)R$^7$ or —(OR$^6$)yOC(O)R$^7$ wherein R$^1$, R$^3$, R$^4$, R$^5$, R$^6$, R$^7$ and y are as defined with respect to Formula I. When R$^2$ is —OR$^1$, the carboxylic esters are diesters, and R is —P-(O)(OR$^3$)$_2$ when the diester is used in a liquid composition containing a fluorine-containing hydrocarbon which also contains other halogens such as chlorine in the hydrocarbon. The diesters may be prepared by the well known esterification reactions on anhydrides or dicarboxylic acids. When R is H, the anhydride is succinic anhydride. Alkyl or alkenyl-substituted succinic anhydrides, wherein R is a hydrocarbyl group, are well known and have been described in the literature. Such dicarboxylic acids and anhydrides can be prepared, for example, by the reaction of an olefin or olefin halide with maleic anhydride. In particular, a polypropylene tetramer can be reacted with maleic anhydride to form a propylene tetramer-substituted succinic anhydride. Similar reactions can be conducted utilizing dimers and trimers of propylene, or dimers, trimers, tetramers of isobutylene.

Carboxylic esters of the type represented by Formulae I and IIF wherein R$^1$ is a hydrocarbyl group are prepared by known processes such as by reaction of a carboxylic acid with an alcohol (R$^1$OH). The alcohols contain from 1 to about 20 carbon atoms and are exemplified by methanol, ethanol, n-propanol, isopropanol, butanol, isobutanol, n-hexanol, 2-ethyl-hexanol, decanol, isodecanol, dodecanol, octadecanol, etc.

The R$^1$ group in any of the above formulae may comprise a mixture of hydrocarbyl groups derived from commercial alcohols. Examples of some preferred monohydric alcohols and alcohol mixtures include the commercially available "Alfol" alcohols marketed by Vista Chemical, Division of E.I. DuPont. Alfol 810 is a mixture containing alcohols consisting essentially of straight-chain, primary alcohols having from 8 to 10 carbon atoms. Alfol 12 is a mixture comprising mostly C$_{12}$ fatty alcohols. Alfol 1218 is a mixture of synthetic, primary, straight-chain alcohols having 12 to 18 carbon atoms. C$_{20}$ alcohols as determined by GLC (gas-liquid-chromatography). The Alfol 22+ alcohols are C$_{18-28}$ primary alcohols having mostly, on an alcohol basis, C$_{22}$ alcohols. These higher Alfol alcohols can contain a fairly large percentage (up to 40% by weight) of paraffinic compounds which can be removed before the reaction if desired.

Another example of a commercially available alcohol mixture is Adol 60 which comprises about 75% by weight of a straight-chain C$_{22}$ primary alcohol, about 15% of a C$_{20}$ primary alcohol and about 8% of C$_{18}$ and C$_{24}$ alcohols. Adol 320 comprises predominantly oleyl alcohol. The Adol alcohols are marketed by Ashland Chemical.

A variety of mixture of monohydric fatty alcohols derived from naturally occurring triglycerides and ranging in chain length of from C$_8$ to C$_{18}$ are available from Procter & Gamble Company. These mixtures contain various amounts of fatty alcohols containing mainly 12, 14, 16, or 18 carbon atoms. For example, CO-1214 is a fatty alcohol mixture containing 0.5% of C$_{10}$ alcohol, 66.0% of C$_{12}$ alcohol, 26.0% of C$_{14}$ alcohol and 6.5% of C$_{16}$ alcohol.

Another group of commercially available mixtures include the "Neodol" products available from Shell Chemical Co. For example, Neodol 23 is a mixture of C$_{12}$ and C$_{13}$ alcohols; Neodol 25 is a mixture of C$_{12}$ to C$_{15}$ alcohols; and Neodol 45 is a mixture of C$_{14}$ and C$_{15}$ alcohols. Neodol 91 is a mixture of C$_9$, C$_{10}$ and C$_{11}$ alcohols. In the Neodols, each alcohol comprises about 25% of a branched isomer and 75% of a straight chain isomer.

Carboxylic esters wherein R$^1$ is a hydrocarbyloxy hydrocarbylene group can be prepared by methods well known to those skilled in the art. For example, such esters can be prepared by esterifying succinic acid or succinic anhydride with a polyoxy alcohol such as represented by the formula

 (IB)

wherein x varies from about 0 to about 16 and n varies from about 1 to about 11. In one preferred embodiment, one R$^1$ group in Formula IIF is a lower alkyl group, and the other R$^1$ is a hydrocarbyloxy hydrocarbylene group. Specific examples of commercially available oxy alcohols of the type represented by the above Formula IB include a number of such alcohols available from Vista under the general trade designation "ALFONIC TM". Specifically, ALFONIC 1412-60 is an ethoxylate of the type represented by the above formula wherein x is about 10–12 and n is an average of about 7. Other oxy alcohols available from Vista include materials wherein x ranges from about 4 to about 16 and n ranges from about 2.5 to about 10.7. Such ethoxylated materials also are available from Shell under the Neodol designation.

Propoxylated alcohols also can be used to form carboxylic esters wherein $R^1$ is a hydrocarbyloxy hydrocarbylene group. Such alcohols are available commercially such as from Union Carbide under the general trade designation "Ucon".

One of the types of carboxylic esters characterized by Formula IIF is further characterized by the formula

$$(R^3O)_2P(O)-\overset{C-C(O)R^2}{\underset{C-COOR^1}{\big|}}\quad\quad (IIG)$$

wherein each $R^3$ is independently a lower alkyl group and $R^1$ and $R^2$ are as defined above with respect to Formula IIF. In one embodiment, compounds of the type represented by Formula IIG are prepared from maleic acid or maleic anhydride, and maleic anhydride generally is used. The maleic anhydride is first reacted with an alcohol or an oxy alcohol, or other hydroxy-containing compound to form a monoester. The monoester intermediate is then reacted with the trialkyl phosphite, $(RO)_3P$ which produces the desired product wherein $R^1=R^3$.

Compounds of the type represented by Formulae IIF and IIG wherein $R^2$ is $-(OR^6)_yN(R^4)C(O)R^7$, wherein $R^6$ is a hydrocarbylene group, $R^4$ is H or a hydrocarbyl group, $R^7$ is a hydrocarbyl group, and y is an integer of from 1 to about 20 are prepared by the above procedure utilizing as the first hydroxy-containing reactant, an oxy alkylene-substituted amide which is represented by the following formula $$R^7C(O)N(R^4)(R^6O)_yH \quad\quad (IV)$$

wherein $R^7$ is a hydrocarbyl group, $R^4$ is H or a hydrocarbyl group, $R^6$ is a hydrocarbylene group, and y is an integer of from 1 to about 20. The hydrocarbylene group $R^6$ generally may be a methylene, ethylene or propylene group, the hydrocarbyl group $R^7$ will contain from 1 to about 20 or more carbon atoms, and $R^4$ is H or a lower alkyl group.

The oxyalkylene-substituted amides (IV) are commercially available compositions. For example, a group of such amides are available from Lonza Chemical Company under the general trade designation "Unamide". A specific example of such amides is Unamide C5 wherein $R^7$ is $C_{12}H_{25}$—, $R^4$ is H, $R^6$ is $-CH_2CH_2-$ and y is 5. The amides of Formula IV also are available under the trade designation "Ethomids" from Akzo Chemie.

In the above Formulae I, IIF and IIG, $R^2$ may be $-NR^4R^5$ wherein $R^4$ and $R^5$ are each independently hydrogen or hydrocarbyl groups. Such amide esters can also be prepared by well-known techniques from dicarboxylic acids or anhydrides by first forming a monoester and then reacting the free carboxyl group with an amine $R^4R^5NH$.

General examples of carboxylic esters of the type represented by Formula IIF are illustrated in the following table.

TABLE II

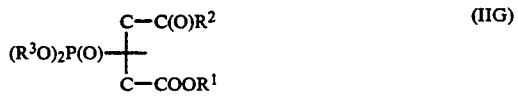
$$R-\overset{C-C(O)R^2}{\underset{C-COOR^1}{\big|}}\quad\quad (IIF)$$

| Ex. | R | $R^1$ | $R^2$ |
|---|---|---|---|
| 1 | H— | $C_2H_5-$ | $-OC_2H_5$ |
| 2 | $C_{12}H_{23}-$ | $CH_3-$ | $-OCH_3$ |
| 3 | $(CH_3O)_2P(O)-$ | $CH_3-$ | $-OC_2H_5$ |
| 4 | $(C_2H_5O)_2P(O)-$ | $C_2H_5-$ | $-OC_2H_5$ |
| 5 | $(C_2H_5O)_2P(O)-$ | $C_2H_5-$ | $-N(C_2H_5)_2$ |
| 6 | $(C_2H_5O)_2P(O)-$ | $C_2H_5-$ | $-(OCH_2CH_2)_5NC(O)C_{12}H_{25}$ |
| 7 | $(C_2H_5O)_2P(O)-$ | $C_2H_5-$ | $-(OC_2H_4)_7O(CH_2)_{11-13}CH_3$ |

The carboxylic esters useful as lubricants in the liquid compositions of the present invention also may be characterized by the formula $$R^1OOCR^{12}XR^{12}COOR^1 \quad\quad (V)$$

wherein each $R^{12}$ is independently a hydrocarbylene group, each $R^1$ is independently a hydrocarbyl group or a hydrocarbyloxy hydrocarbylene group, and X is O, S or $NR^8$ wherein $R^8$ is H, hydrocarbyl or $R^9C(O)-$, and $R^9$ is a hydrocarbyl group. The hydrocarbyl groups $R^8$ and $R^9$ may each independently contain from 1 to about 20 carbon atoms. The hydrocarbylene groups $R^{12}$ may contain any number of carbon atoms provided that the carboxylic ester is soluble in the fluorine-containing hydrocarbon. Generally, the hydrocarbylene groups contain from 1 to about 10 carbon atoms. The hydrocarbyl group $R^1$ generally may contain from 1 to about 20 carbon atoms, and the hydrocarbyl group may be a branched or a straight chain hydrocarbyl group. The hydrocarbyloxy hydrocarbylene groups may contain from 1 to about 50 carbon atoms, and these groups also may be straight chain or branched chain. The branched chain hydrocarbyl and hydrocarbyloxy hydrocarbylene groups generally provide esters which are more soluble than esters containing the straight chain groups. Specific examples of $R^1$ alkyl groups include ethyl, propyl, n-butyl, isobutyl, n-pentyl, 2,2,4-trimethylpentyl, n-hexyl, 2-ethylhexyl, etc. Examples of $R^7$ alkylene groups include ethylene, methyl ethylene, propylene, n-butylene, n-hexylene, etc.

The dicarboxylic acid esters of the type represented by Formula V can be prepared by methods well known to those skilled in the art. For example, the dicarboxylic acid esters can be prepared by esterification of the corresponding dicarboxylic acids, many of which are commercially available. Specific examples of dicarboxylic acid materials which can be esterified to form diesters of the type represented by Formula V include: thiodiglycolic acid; 3,3'-thiodipropionic acid; diglycolic acid; 3,3'-oxydipropionic acid, etc. Carboxylic esters of the type represented by Formula V are illustrated in the following Table III.

TABLE III

| | | $R^1OOCR^{12}XR^{12}COOR^1$ | | (V) |
|---|---|---|---|---|
| Ex. | X | $R^{12}$ | $R^1$ | |
| 8 | O | $-CH_2CH_2-$ | $n-C_3H_7-$ | |
| 9 | O | $-CH_2CH_2CH_2-$ | isobutyl | |
| 10 | O | $-CH_2CH_2-$ | 2-methylpentyl | |
| 11 | S | $-CH_2CH_2-$ | $C_2H_5-$ | |
| 12 | S | $-CH_2CH_2CH_2-$ | 2,2,4-trimethylpentyl | |

TABLE III-continued

| | | $R^1OOCR^{12}XR^{12}COOR^1$ | (V) |
|---|---|---|---|
| Ex. | X | $R^{12}$ | $R^1$ |
| 13 | NH | $-CH_2CH_2-$ | $n\text{-}CH_3H_7-$ |

The carboxylic esters useful as lubricants (B) in the liquid compositions of the present invention also may be characterized by the following formula

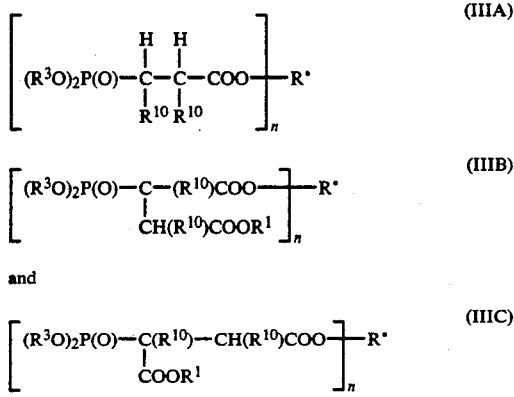

wherein $R^o$ is an alkylene group;

$R^1$ is a hydrocarbyl group or a hydrocarbyloxy hydrocarbyl group and $R^1$ may be the same as $R^3$;

$R^3$ is independently a hydrocarbyl group;

$R^{10}$ is independently H or a hydrocarbyl group; and n is an integer from 2 to about 6.

The liquid compositions of the invention are useful particularly as refrigeration liquids in refrigerators and air-conditioners including auto, home and industrial air-conditioners.

The alkylene group $R^o$ may be a straight chain or a branched chain alkylene group such as ethylene, propylene, methyl ethylene, butylene, etc. The $R^o$ group may contain two or more hydroxyl groups. The groups $R^1$, $R^3$ and $R^{10}$ correspond to the same groups as found in Formulae IIF and IIG described above, and the discussion of such groups with respect to Formulae IIF and IIG is equally applicable to these same groups in Formulae IIIA, IIIB and IIIC.

Phosphorus-containing compositions characterized by Formula IIIA may be prepared by the reaction of an alpha,beta-unsaturated carboxylic acid with a polyhydroxy compound to form an ester which may then be reacted with a dialkyl phosphite $(R^3O)_2P(O)H$, in the presence of a free radical generator. An excess of the alpha,beta-unsaturated carboxylic acid can be reacted with a polyhydroxy compound resulting in the reaction with more than one hydroxy group of the polyhydroxy compound, and, therefore, n may be an integer of from 2 to about 6 depending upon the number of hydroxy groups in the polyhydroxy reactant and the amount of carboxylic acid utilized in the reaction. Examples of useful polyols include glycerol, pentaerythritol, dipentaerythritol, etc. Examples of alpha,beta-unsaturated carboxylic acids which may be reacted with the polyhydroxy compounds include acyclic acid and substituted acrylic acids such as methacrylic acid, crotonic acid, etc.

Esters of the type represented by Formulae IIIB and IIIC are obtained from alpha, beta-unsaturated dicarboxylic acids or anhydrides by reaction with a polyhydroxy compound to produce one or more half-esters. These are subsequently treated with a trialkyl phosphite in equimolar amounts corresponding to the moles of alpha, beta-unsaturated dicarboxylic acid or anhydride used. The product of these reactions corresponds to Formulae IIIB and IIIC where $R^1=R^3$. It is believed that the product is predominantly a product of Formula IIIB.

The following examples illustrate the preparation of some of the specific carboxylic esters identified in Tables II and III and other esters represented by the formulae above which are useful in the homogeneous liquid compositions of the present invention.

EXAMPLE 2

A mixture of 532 parts (2 moles) of propylene tetramer-substituted succinic anhydride, 300 parts of methanol and 30 parts of Amberlyst 15, a catalyst from Rohm & Haas, is prepared and stirred at room temperature for 6 hours, and thereafter heated to 70° C. and maintained at this temperature overnight. Methanol/water is then removed, and additional methanol is added and the reaction stirred at 90° C. for 4 hours. The procedure of adding methanol and heating at 90° C. for 4 hours is repeated three times to yield the desired product.

EXAMPLE 4

A reactor is charged with 392 parts (4 moles) of maleic anhydride and 202 parts of ethanol, and the mixture is heated to 65° C. At about 60° C., an exotherm begins and the mixture reaches a temperature of about 85° C. When the exotherm is completed, the mixture is heated to 95° C. and maintained at this temperature for 3 hours. A portion of this mixture (187 parts, 1.26 equivalents) is charged to a reaction vessel and heated to 75° C. whereupon 210 parts (1.26 equivalents) of triethyl phosphite are added over a period of 1.5 hours while maintaining the temperature at about 70°-80° C. When all of the phosphite is added, the mixture is heated at 75° C. for an additional 5 hours, vacuum stripped to 160° C. at 20 mm.Hg., and filtered. The filtrate is the desired product containing 10.82% phosphorus (theory, 10.0).

EXAMPLE 6

Into a reaction vessel there are charged 196 parts (2.0 equivalents) of maleic anhydride, 120 parts of toluene and 660 parts of Unamide C-5 available from Lonza Chemical Company. The above prepared mixture is heated to 60° C. to dissolve the maleic anhydride, and then the mixture is heated to 95° C. and maintained at this temperature for 4 hours. After cooling to 60° C., an additional 6.6 parts of Unamide C-5 are added and the mixture is heated to 95° C. to finish the reaction. Triethyl phosphite (299 parts) are then added dropwise. The addition is completed in about 2.5 hours and the mixture is maintained at 90° C. for 2 hours. The reaction mixture is stripped by heating to 140° C. at 30 mm.Hg. The residue is filtered through a filter pad, to give the desired product containing 4.55% phosphorus (theory, 4.8) and 1.8% nitrogen (theory, 2.4).

EXAMPLE 7

A mixture of 49 parts (0.5 equivalent) of maleic anhydride and 262 parts (0.5 equivalent) of Alfonic 1412-60 is prepared and heated with stirring to 60° C. to dissolve the maleic anhydride. An exothermic reaction occurs raising the temperature to 85° C., and the mixture is maintained at 90° C. for one hour. After cooling to about 80° C., 83 parts of triethyl phosphite are added dropwise to the reaction mixture, and the addition is completed in about 2.5 hours. The reaction mixture is maintained at 90° C. for an additional 2 hours, and after heating to about 150° C., the reaction mixture is cooled and filtered using a filter aid. The filtrate is the desired product containing 3.55% phosphorus (theory, 3.9).

EXAMPLE 12

A reaction flask is charged with 534 parts (3 moles) of thiodipropionic acid, 858 parts (6.6 moles) of 2,2,4-trimethylpentanol, 600 parts of xylene, and 12 parts of para-toluene sulfonic acid. The mixture is heated to reflux (110°–160° C.) for 4 hours while removing water. The mixture is cooled and 7.2 parts of a 50% aqueous sodium hydroxide are added to neutralize the catalyst. The reaction mixture is stripped at 90°–150° C./10 mm., and the residue is filtered at 80° C. through a filter pad. The filtrate is the desired product containing 7.59% sulfur (theory, 7.93).

EXAMPLE 14

A reactor is charged with 144 parts (2 moles) of acrylic acid, and thereafter, 332 parts of triethylphosphite (2 moles) are added rapidly dropwise. An exothermic reaction occurs, and the reaction temperature is maintained at about 45° C. using a cold water bath. The reaction mixture is raised to 70° C. and maintained at this temperature for about 2 hours to complete the reaction. The reaction product is vacuum stripped at 85° C./1 mm.Hg. The residue is the desired product containing 13.00% phosphorus (theory 13.03).

EXAMPLE 15

The ethyl ester obtained in Example 14 is transesterified with a commercial alcohol mixture containing 8 to 10 carbon atoms (Alfol 810 from Vista). The reaction vessel is charged with 119 parts (0.5 mole) of the product of Example 14 and 74 parts (0.5 mole) of Alfol 810, and the mixture is stirred under a slow nitrogen purge followed by heating to 160° C. over a period of 0.5 hour. At about 50° C., 0.1 part of sodium metal is added. The mixture is maintained at 160°–170° C. while about 23 parts of a colorless liquid slowly distills into the water trap attached to the reaction vessel. The reaction mixture is poured into 100 parts of toluene and washed three times with 100 parts of water. The washed product is stripped at 100° C./1 mm.Hg., and the residue is the desired product containing 8.91% phosphorus (theory 9.14).

EXAMPLE 16

A reaction vessel is charged with 72 parts (1 mole) of acrylic acid, and while stirring, 503 parts (1 mole) of tridecylphosphite are added dropwise. The temperature slowly rises to about 50° C., thereafter heat is applied to raise the reaction temperature to 80° C. for 5 hours. Unreacted material is stripped off at 95°–100° C./10 mm.Hg. The residue is the desired product containing 5.39% phosphorus (theory 5.39).

EXAMPLE 17

A mixture of 72 parts (0.3 mole) of the product of Example 14 and 87 parts (0.3 mole) of Armeen O (Armak) is prepared, and the mixture is heated to 100° C. under a nitrogen purge. At 100° C., 0.2 part of sodium methoxide is added and the reaction mixture is heated slowly to 165°–170° C. The mixture is maintained at this temperature for about two hours and about 7 parts of ethanol are evolved and recovered. The residue is the desired product.

EXAMPLE 18

A mixture of 119 parts (0.5 mole) of the product of Example 14 and 52.5 parts (0.5 mole) of 2-amino-2-methyl-1,3-propanediol is prepared and heated to 160°–175° C. over a period of 0.5 hour. The mixture is maintained at this temperature with stirring under a slow nitrogen purge while removing volatile materials. The residue is the desired product containing 10.21% phosphorus (theory 10.44) and 4.80% nitrogen (theory 4.71).

EXAMPLE 19

A mixture of 196 parts (2 moles) of maleic anhydride and 102 parts (2.2 moles) of ethanol is heated to 65° C. where an exothermic reaction occurs. The mixture is maintained at 95° C. for two hours and then is cooled to 75° C. whereupon 332 parts (2 moles) of triethylphosphite are rapidly added in a dropwise manner. A cold water bath is used to maintain the reaction temperature at 75°–80° C. during the addition of the triethylphosphite and for an additional 5 hours after all of the triethylphosphite is added. The mixture is vacuum stripped at 100° C./3 mm., and the residue is fractionally distilled through a helix-packed column, and the following fractions are recovered.

(A) b.p. 100°–135° C./0.2 mm; 77 parts of colorless liquid;
(B) b.p. 135°–137° C./0.2 mm; 108 parts of colorless liquid; and
(C) b.p. 137°/0.2 mm; 282 parts of colorless liquid. The B and C fractions comprise the desired product. Fraction C contains 10.42% phosphorus (theory 10.00).

EXAMPLE 20

A mixture of 217 parts (1 mole) of Alfol 1218 and 98 parts (1 mole) of maleic anhydride is prepared and heated to 120° C. for 3 hours. The mixture is cooled to 60° C., and 503 parts (1 mole) of tridecylphosphite are added. The reaction mixture is heated to 90° C. for 4 hours and stripped at 90° C./10 mm. The residue is the desired product containing 3.80% phosphorus (theory 3.79).

EXAMPLE 21

A mixture of 98 parts (1 mole) of maleic anhydride and 78 parts (1.3 moles) of isopropanol is prepared, and an exothermic reaction occurs raising the temperature of the mixture to 60°–70° C. This mixture is treated with 166 parts (1 mole) of triethylphosphite and the mixture is then maintained at 90°–100° C. for 4 hours. After stripping at 120° C./5–10 mm.Hg., the residue is the desired product.

EXAMPLE 22

(A) A mixture of 588 parts (6 moles) of maleic anhydride and 786 parts (6 moles) of 2-ethylhexanol is prepared by melting the maleic anhydride in the alcohol at 60° C. The mixture is stirred with nitrogen sparging and heated to 95° C. whereupon an exothermic reaction occurs to 105° C. over 5 minutes. The mixture is returned to 95° C. and maintained at this temperature for 2 hours. Sodium acetate (3.41 parts) is added at 95° C., and the mixture is maintained at this temperature for an additional 2.25 hours. After cooling to about 35° C., the liquid is filtered to yield a clear, beige liquid product which is the desired monoester of maleic acid.

(B) Into a reactor there are charged 458 parts (2 moles) of the monoester prepared in (A), and while stirring at room temperature, 500 parts (2 moles) of tributylphosphite are added dropwise. An intermediate exothermic reaction occurs from about 28° C. to 40° C. over 5 minutes as 30 grams of the phosphite are added. The exothermic reaction reaches 57° C. in another 5 minutes when a total of 100 grams of the phosphite has been added. A water bath is alternately placed under the reactor and removed as needed to maintain the reaction mixture between 50°–60° C. during the remainder of the tributylphosphite addition. The total time required for the addition is about 1.5 hours. Thereafter, the reaction mixture is cooled to room temperature and stirred for 4 hours. After cooling overnight, 36.3 parts of tributylphosphite are added to the reaction mixture at 28° C. without any exotherm. The mixture is stirred at this temperature for 2.5 hours and for 3 hours at 65° C. Unreacted tributylphosphite is removed from the reaction mixture over 4 hours by stripping at 180° C./13 mm.Hg. The residue, after stripping, is cooled to 25° C. and filtered through a cloth pad with filter aid to yield a filtrate which is the desired product containing 6.17% phosphorus (theory 6.47).

EXAMPLE 23

A reactor is charged with 418 parts (1 mole) of tris(2-ethylhexyl) phosphite, and while stirring at 25° C., 229 parts (1 mole) of the monoester prepared in Example 22A are added dropwise over 40 minutes. The reaction is exothermic from about 24° C. to 55° C. over the course of the addition. The reaction mixture is cooled at 34° C. with stirring 1.5 hours after completing the addition. The reaction mixture is stripped over 4 hours to 200° C./1.0 mm.Hg. to remove any unreacted phosphite. The residue, after stripping, is cooled under vacuum to 50° C. and then to 25° C. The cooled product is filtered through a cloth pad with filter aid at room temperature to yield the desired product containing 4.32% phosphorus (theory 4.79).

EXAMPLE 24

(A) A mixture of 588 parts (6 moles) of maleic anhydride and 444 parts. (6 moles) of isobutanol is prepared by melting the maleic anhydride into the alcohol at 65° C. The solution is cooled under nitrogen to 30° C., and 2.58 parts of sodium acetate are added. The mixture is heated with stirring with a nitrogen sparge over 0.75 hour to about 95° C. where the mixture is maintained for one hour before cooling overnight under nitrogen. The temperature of the mixture is returned to 95° C. under nitrogen for an additional 5 hours. After cooling to 25° C., the liquid is filtered through a cloth pad with a filter aid to yield a clear, water-white liquid product which is the desired monoisobutyl ester.

(B) A reactor is charged with 500 parts (2 moles) of tributylphosphite which is stirred under a nitrogen sparge while 344 parts (2 moles) of the monoester prepared in (A) above are added dropwise. An exothermic reaction occurs and the temperature is maintained at about 48° C. by adding the monoester over a period of 1.75 hours. Upon completion of the addition of the monoester, the reaction mixture is cooled to 30° C. without external cooling over a period of 2 hours. The mixture then is heated over a period of 3 hours to a maximum temperature of 120° C. to complete the reaction and cooled under nitrogen to 25° C. overnight. The reaction mixture is slowly heated to a maximum temperature of 186° C./13 mm.Hg. while a clear water-white liquid is stripped from the reaction mixture. A red-brown residue after stripping is allowed to cool under vacuum to 80° C. and then cooled to 25° C. at atmospheric pressure. The liquid is filtered through a cloth pad with a filter aid, and the filtrate is the desired product containing 7.52% phosphorus (theory 7.35).

EXAMPLE 25

A reactor is charged with 418 parts (1 mole) of tris(2-ethylhexyl) phosphite, and 172 parts (1 mole) of the monoester prepared in Example 24A are added with stirring under nitrogen over a period of 1.25 hours. An exothermic reaction raises the temperature of the mixture from 23° C. to 51° C. during the addition. Upon completion of the addition of the monoester, the liquid is stirred for 0.5 hour to 45° C., and then externally heated over 0.5 hour to 118° C. The mixture is maintained at this temperature with gradual darkening for 6.5 hours. After cooling under nitrogen overnight, the liquid is stripped of volatiles at 192° C./11 mm.Hg. The residue, after stripping, is cooled under vacuum to 55° C. and then at atmospheric pressure to 25° C. The cooled residue is filtered through a cloth pad and a filter aid to yield a clear, red-brown liquid which is the desired product containing 4.60% phosphorus (theory 5.25).

EXAMPLE 26

(A) A mixture of 490 parts (5 moles) of maleic anhydride and 720 parts (5 moles) of Alfol 810 is prepared by melting the maleic anhydride into the alcohol at 60° C. Sodium acetate (3 parts) is then added with stirring, and the liquid is heated under a nitrogen sparge to 95°–97° C. and maintained at this temperature for 3 hours. After cooling to 25° C. overnight, the mixture is reheated to 97° C. and maintained at this temperature for 7 hours. The liquid is cooled to about 55° C. under nitrogen and filtered through a cloth pad with filter aid to yield a clear, beige liquid product which contains the desired monoester.

(B) A reactor is charged with 500 parts (2 moles) of tributylphosphite, and 484 parts (2 moles) of the monoester prepared in (A) are added dropwise over 3 hours while maintaining the exothermic reaction at about 45° C. during the last two hours of addition. The reaction mixture is stirred an additional hour upon completion of the addition of the monoester, and the reaction temperature at this time is about 30° C. After cooling overnight under nitrogen, the liquid is heated with stirring and nitrogen sparge to 120° C. and maintained at this temperature for 5 hours. Unreacted tributyl phosphite and other volatile materials are removed by stripping the mixture at 184° C./10 mm.Hg. The residue, after stripping, is cooled under vacuum to 35° C. and filtered through a cloth pad with a filter aid to yield a clear, red-brown liquid which is the desired product containing 5.28% phosphorus (theory 6.30).

EXAMPLE 27

(A) A mixture of 490 parts (5 moles) of maleic anhydride and 790 parts (5 moles) of isodecyl alcohol is prepared by melting the maleic anhydride into the alcohol at 60° C. Sodium acetate (3.2 parts) is added to the mixture which is then heated with stirring and nitrogen sparged to about 95° C. The mixture is maintained at this temperature for 7 hours and allowed to cool overnight. The liquid is filtered through a cloth pad with filter aid to yield a clear, water-white liquid product which contains the desired monoester.

(B) A reaction vessel is charged with 500 parts (2 moles) of tributylphosphite, and 512 parts (2 moles) of the monoester prepared in (A) is added dropwise over 3 hours with stirring. An exothermic reaction occurs, and the reaction temperature reaches about 39° C. after about ⅔ of the ester has been added. When all of the ester has been added, the reaction mixture is stirred an additional hour as the temperature of the mixture decreases to about room temperature. External heating is applied to raise the temperature of the reaction mixture to 120° C., and the mixture is maintained at this temperature for 3 hours before cooling under nitrogen overnight. The liquid is stripped of any volatile materials over 4 hours to a maximum temperature of 180° C./7 mm.Hg. The residue in the flask, after stripping, is cooled to 25° C. and filtered through a cloth pad with filter aid to yield a clear, burgundy liquid which is the desired product containing 4.54% phosphorus (theory 6.13).

EXAMPLE 28

A reactor is charged with 418 parts (1 mole) of tris(2-ethylhexyl) phosphite, and while stirring under nitrogen, 256 parts (1 mole) of the monoester prepared in Example 27A are added dropwise over 2 hours. An exothermic reaction occurs increasing the temperature of the mixture to 45° C. after 0.75 hour of addition. The mixture then is heated by external means to 120° C. and maintained at this temperature for 3.5 hours. After cooling overnight under nitrogen, the liquid is again heated to 120° C. under nitrogen and maintained at this temperature for 3.5 hours. The reaction mixture is stripped of volatile materials over 4 hours at 200° C./11 mm.Hg., and the residue, after cooling to room temperature is filtered to yield a clear orange-brown liquid which is the desired product containing 4.56% phosphorus (theory 4.60).

EXAMPLE 29

A mixture of 77.5 parts (0.25 mole) of the phosphorus-containing diester prepared in Example 19 and 72.5 parts (0.25 mole) of Armeen O is prepared and heated to 100° C. whereupon 0.2 part of sodium methoxide is added. This mixture is heated at 160°-165° C. for one hour and thereafter at 170°-175° C. for 3 hours as ethanol is evolved and removed. The residue is the desired amide ester.

EXAMPLE 30

A mixture of 680 parts (2 moles) of dioctyl maleate and 414 parts (3 moles) of diethyl phosphite is heated to 130° C. whereupon 6.9 parts of butyl peroxide are added in ten portions at about 30-minute intervals over 5 hours. The mixture is maintained at 135° C. for an additional 8 hours and stripped at 155°-200° C./28 mm.Hg. The residue is filtered through a filter aid, and the filtrate is the desired product containing 4.88% phosphorus (theory 5.05).

EXAMPLE 31

A mixture of 196 parts (2 moles) of maleic anhydride and 101 parts (2.2 moles) of ethyl alcohol is heated to dissolve the maleic anhydride in the ethanol. An exothermic reaction occurs raising the temperature of the mixture to 105° C. The mixture is cooled to about 95° C. and maintained at this temperature with external cooling for 3 hours. After cooling overnight, the mixture is heated to 90° C., and 332 parts (2 moles) of triethyl phosphite are added in a dropwise manner over a period of 2.75 hours. when all of the phosphite is added, the mixture is maintained at 90°-95° C. for about 3 hours and for an additional 2 hours while vacuum stripping to 150° C. at 30 mm.Hg. An infrared analysis of the distillate indicates the presence of a large amount of product, and the distillate is returned to the reaction vessel. The contents of the reaction vessel are heated to 80° C., and 258 parts (2 moles) of 2-ethylhexyl amine are added. The temperature of the mixture is raised to 150° C. under nitrogen and maintained at this temperature for about 5.5 hours while removing distillate. After cooling overnight, the mixture is again heated to 150° C. and maintained at this temperature for 5 hours while removing additional distillate. The mixture is vacuum stripped to 15 mm.Hg. at 120° C. The residue is filtered through a filter aid and the filtrate is the desired product containing 8.3% phosphorus (theory 7.9) and 3.6% nitrogen (theory 3.5).

EXAMPLE 32

A mixture of 49 parts (0.5 mole) of maleic anhydride and 141 parts (0.5 mole) of Neodol 91-2.5 is heated without stirring to 60° C. whereupon the mixture exotherms to about 80° C. While stirring, the mixture is heated to about 95° C. and maintained at this temperature for 2 hours. After cooling to 75° C., 83 parts (0.5 mole) of triethyl phosphite is added dropwise as the temperature is maintained at 75°-80° C. by heating and cooling the reaction vessel as necessary. When all of the phosphite is added, the mixture is maintained at 75° C. for a total of about 6 hours and vacuum stripped to 120° C. at 10 mm.Hg. The residue is filtered through a filter aid, and the filtrate is the desired product containing 5.3% phosphorus (theory 5.68).

EXAMPLE 33

A mixture of 695 parts (1.45 moles) of di-$C_{12-14}$ fumarate and 427 parts (2.2 moles) of dibutylhydrogen phosphite is heated to 130°-135° C., and 5 parts of tertiary butyl peroxide are added in 10 equal portions over a period of 5 hours at 30-minute intervals. The mixture is maintained at 135° C. for a total of 10 hours and stripped at 155°-160° C./2 mm.Hg. to yield an orange-red viscous liquid which is the desired product containing 2.91% phosphorus.

EXAMPLE 34

The general procedure of Example 32 is repeated except that the Neodol 91-2.5 is replaced by an equivalent amount of Neodol 25-3.

EXAMPLE 35

The general procedure of Example 32 is repeated except that the Neodol 91-2.5 is replaced by an equivalent amount of Neodol 23-1.

The carboxylic ester lubricants (B) described above are soluble in the fluorine-containing hydrocarbons and, in particular, in the fluorohydrocarbons such as 1,1,1,2-tetrafluoroethane. The lubricants are soluble over a wide temperature range and, in particular, at low temperatures. The solubility of the lubricants in fluorohydrocarbons such as 1,1,1,2-tetrafluoroethane at low temperatures is determined in the following manner. The lubricant (0.5 gram) is placed in a thick-walled glass vessel equipped with a removable pressure gauge. The tetrafluoroethane (4.5 grams) is condensed into the cooled ($-40°$ C.) glass vessel, and the contents are warmed to the desired temperature and mixed to determine if the lubricant is soluble in the tetrafluoroethane. If soluble, the temperature of the mixture is reduced until a separation and/or precipitate is observed. The results of this solubility test conducted with several examples of the carboxylic ester lubricants of the present invention are summarized in the following Table IV.

TABLE IV

| Liquid Containing Product of Example | Solubility °C. (ppt.) |
|---|---|
| 4 | $-40$ |
| 7 | $-20$ |
| 12 | $-25$ |
| 31 | $-40$ |
| 32 | $-40$ |
| 35 | $-15$ |

The liquid compositions of the present invention comprise a major amount of a fluorine-containing hydrocarbon and a minor amount of at least one soluble organic lubricant comprising at least one carboxylic ester of the types described above. By "major amount" is meant an amount greater than 50% by weight such as 50.5%, 70%, 99%, etc. The term "minor amount" includes amounts less than 50% by weight such as 1%, 5%, 20%, 30% and up to 49.9%. In one embodiment, the liquid compositions of the present invention will comprise from about 70 to about 99% of the fluorine-containing hydrocarbon (A) and from about 1 to about 30% by weight of the lubricant (B). In other embodiments, the liquid compositions of the present invention may contain from about 5 to about 20% by weight of the lubricant (B).

The liquid compositions of the present invention are characterized as having improved thermal and chemical stability over a wide temperature range. Other additives, if soluble in the liquid, known to be useful for improving the properties of halogen-containing hydrocarbon refrigerants can be included in the liquid compositions of the present invention to improve the characteristics of the liquid as a refrigerant. However, hydrocarbon oils such as mineral oil generally are not included in and are most often excluded from the liquid compositions of the invention, particularly when the fluorine-containing hydrocarbon contains no other halogen. Polyglycols and alkyl ethers which have been suggested in the prior art as useful solvents for fluorine-containing hydrocarbons are not required in the liquid compositions of the present invention and are generally omitted from the liquid compositions.

The additives which may be included in the liquid compositions of the present invention to enhance the performance of the liquids include extreme-pressure and anti-wear agents, oxidation and thermal-stability improvers, corrosion-inhibitors, viscosity-index improvers, pour point and/or floc point depressants, detergents, dispersants, anti-foaming agents, viscosity adjusters, etc. As noted above, these supplementary additives must be soluble in the liquid compositions of the invention. Included among the materials which may be used as extreme-pressure and anti-wear agents are phosphates, phosphate esters, phosphites, thiophosphates such as zinc diorganodithiophosphates, dithiocarbamates, chlorinated waxes, sulfurized fats and olefins, organic lead compounds, fatty acids, molybdenum complexes, borates, halogen-substituted phosphorous compounds, sulfurized Diels Alder adducts, organic sulfides, metal salts of organic acids, etc. Stearically hindered phenols, aromatic amines, dithiophosphates, phosphites, sulfides and metal salts of dithioacids are useful examples of oxidation and thermal stability improvers. Compounds useful as corrosion-inhibitors include organic acids, organic amines, organic phosphates, organic alcohols, metal sulfonates, organic phosphites, etc. VI improvers include polyolefins such as polybutene, polymethacrylates, etc. Pour point and floc point depressants include polymethacrylates, ethylene-vinyl acetate copolymers, succinamic acid-olefin copolymers, ethylene-alpha olefin copolymers, etc. Detergents include sulfonates, long-chain alkyl-substituted aromatic sulfonic acids, phosphonates, phenylates, metal salts of alkyl phenols, alkyl phenol-aldehyde condensation products, metal salts of substituted salicylates, etc. Silicone polymers are a well known type of anti-foam agent. Viscosity adjusters are exemplified by polyisobutylene, polymethacrylates, polyalkyl styrenes, naphthenic oils, alkyl benzene oils, polyesters, polyvinyl chloride, polyphosphates, etc.

The liquid compositions of the present invention are particularly useful as refrigerants in various refrigeration systems which are compression-type systems such as refrigerators, freezers, and air-conditioners including automotive, home and industrial air-conditioners. The following examples are illustrative of the liquid compositions of the present invention.

|  | Parts by Wt. |
|---|---|
| Example A | |
| 1,1,1,2-tetrafluoroethane (R134a) | 90 |
| Lubricant of Example 2 | 10 |
| Example B | |
| 1,1,2,2-tetrafluoroethane | 85 |
| Lubricant of Example 4 | 15 |
| Example C | |
| 1,1,1,2-tetrafluoroethane | 95 |
| Lubricant of Example 6 | 5 |
| Example D | |
| R134a | 80 |
| Product of Example 7 | 20 |
| Example E | |
| R134a | 85 |
| Product of Example 4 | 15 |

The phosphorus-containing carboxylic esters of the present invention are useful also as synthetic lubricants, and particularly as synthetic lubricants for lubricating metal parts. The phosphorus-containing carboxylic esters are particularly useful as lubricants in formulations for use at low temperatures, as in satelllites, polar regions and deep ocean sensing and exploration devices.

The phosphorus-containing carboxylic ester compositions useful as synthetic lubricants are those characterized by the following formulae

(IA)

-continued

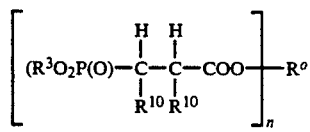 (IIIA)

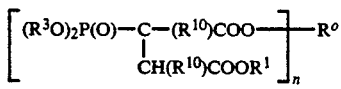 (IIIB)

and

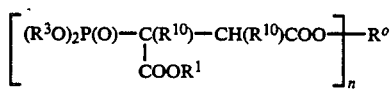 (IIIC)

wherein
R+ is a hydrocarbylene group substituted with a $-P(O)(OR^3)_2$ group;
Z is $-COOR^1$, $-C(O)NR^4R^5$, $-C(O)(OR^6)yN(R^4)-C(O)R^7$, $-C(O)(OR^6)yOC(O)R^7$, $-CN$, $-CHO$, or $-C(O)R^7$;
$R^o$ is an alkylene group;
$R^1$ is a hydrocarbyl group or a hydrocarbyloxy hydrocarbyl group and Ri may be the same as $R^3$;
$R^3$ is independently a hydrocarbyl group;
$R^4$ and $R^5$ are each independently H or hydrocarbyl groups;
$R^6$ is a hydrocarbylene group;
$R^7$ is a hydrocarbyl group;
y is an integer from 1 to about 20;
$R^{10}$ is independently H or a hydrocarbyl group;
$R^{11}$ is H or $-COOR^1$; and
n is an integer from 2 to about 6,
provided that at least one of Z or $R^{11}$ in Formula IA is a $COOR^1$ group.

Formula IA differs from Formula I described previously in that R+ is a hydrocarbylene group substituted with a $-P(O)(OR^3)_2$ group whereas R* in Formula I may be a hydrocarbylene group which is not substituted with the phosphorus group. In addition, the phosphorus-containing ester compositions represented by Formulae IA and IIIA-C which are to be utilized as synthetic lubricants may contain aromatic unsaturation, and in particular, $R^{10}$ in Formula III as well as in the following Formula II may be an aromatic group such as a phenyl group.

$$RC(R^{10})(R^{11})-C(R^{10})(R)Z \qquad (II)$$

wherein R, $R^{10}$, $R^{11}$ and Z are as defined with respect to Formula II above. The phosphorus-containing carboxylic esters of Formula IA may be further characterized by Formula IIF

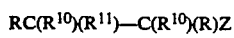 (IIF)

wherein $R^1$, $R^2$ and $R^3$ are as defined above with respect to Formula IIF. Compositions of the type represented by Formula IIF can be prepared by methods described previously. Briefly, the esters are prepared by the addition of a trialkyl phosphite to an alpha, beta-unsaturated carboxylic acid which may be represented by the formula $$R^2C(O)C=C(COOH)$$

Specific examples of the phosphorus-containing carboxylic esters which are useful as synthetic lubricants include the various phosphorus-containing carboxylic esters described above with respect to the liquid compositions of the invention and which have been specifically illustrated in, for example, Examples 4, 6, 7, 14, etc.

The phosphorus-containing carboxylic acid esters of the present invention are particularly useful as specialty lubricants under low temperature conditions since the esters are characterized as having excellent low temperature pour points and desirable viscosities over a wide temperature range even though characterized by high VI values. The low pour points of the phosphorus-containing carboxylic esters of the present invention make them particularly suitable candidates for lubricants used in polar regions as well as in space. For example, the phosphorus-containing carboxylic esters may be particularly useful as lubricants in satellites and exploration vehicles.

The desirable low pour point and viscosity characteristics of several of the phosphorus-containing carboxylic esters illustrated in the above specific examples are summarized in the following table.

TABLE V

| Product of Example | Pour Point (°C.) | Viscosity @40° C.(CST) | Viscosity @100° C.(CST) | VI |
|---|---|---|---|---|
| 15 | <−70 | 11.5 | 3.18 | 149 |
| 20 | <−70 | 28.8 | 5.57 | 147 |
| 23B | <−50 | 11.05 | 2.74 | 109 |
| 27B | −46 | 10.69 | 2.904 | 124 |
| 29 | <−50 | 17.10 | 3.72 | 104 |

Characteristics of P-Containing Esters

Although the phosphorus-containing compositions of the types represented by Formulae IA and IIIA-C generally exhibit desirable extreme pressure and anti-wear properties, the performance of the esters as synthetic lubricants generally may be improved by the use of other additives in combination with the esters of the present invention. Such additives include, for example, additives capable of improving the oxidation stability and/or anti-wear and/or extreme pressure properties of the lubricant as well as detergents, dispersants of the ash-producing or ashless type, color stabilizers, antifoam agents, etc.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the coolant fluid compositions of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in many U.S. patents including U.S. Pat. Nos. 3,219,666 and 4,234,435.

(2) Reaction products of relatively high molecular weight aliphatic or alicyclic halides with amines, preferably polyalkylene polyamines. These may be characterized as "amine dispersants" and examples thereof are described for example, in U.S. Pat. No. 3,454,555.

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in U.S. Pat. No. 3,980,569 are illustrative.

(4) Products obtained by post-treating the carboxylic amine or mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in U.S. Pat. Nos. 3,493,520 and 3,704,308.

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in U.S. Pat. No. 3,702,300. The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, dibutyl tetrasulfide, sulfurized methyl ester of oleic acid, sulfurized alkylphenol and sulfurized dipentene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The above additives can be added directly to the synthetic lubricants or they may be diluted with a substantially inert normally liquid organic diluent, including the synthetic lubricant, to form additive concentrates. These concentrates usually contain from about 5 to about 90% by weight of the chemical additives of the type described above. The remainder of the concentrate is the diluent.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A method for lubricating metal parts which comprises contacting said parts with a lubricant comprising at least one phosphorus-containing composition characterized by the formulae

|  | Parts by Wt. |
|---|---|
| Example A |  |
| 1,1,1,2-tetrafluoroethane (R134a) | 90 |
| Lubricant of Example 2 | 10 |
| Example B |  |
| 1,1,2,2-tetrafluoroethane | 85 |
| Lubricant of Example 4 | 15 |
| Example C |  |
| 1,1,1,2-tetrafluoroethane | 95 |
| Lubricant of Example 6 | 5 |
| Example D |  |
| R134a | 80 |
| Product of Example 7 | 20 |
| Example E |  |
| R134a | 85 |
| Product of Example 4 | 15 | wherein
R+ is a hydrocarbylene group substituted with a —P(O)(OR$^3$)$_2$ group;
Z is —COOR$^1$, —C(O)NR$^4$R$^5$, —C(O)(OR$^6$)yN(R$^4$)-C(O)R$^7$, —C(O)(OR$^6$)yOC(O)R$^7$, —CN, —CHO, or —C(O)R$^7$;
R$^o$ is an alkylene group;
R$^1$ and R$^3$ are each independently lower alkyl groups;
R$^4$ and R$^5$ are each independently H or hydrocarbyl groups;
R$^6$ is a hydrocarbylene group;
R$^7$ is a hydrocarbyl group;
y is an integer from 1 to about 20;
R$^{10}$ is independently H or a hydrocarbyl group;
R$^{11}$ is H or —COOR$^1$; and
n is an integer from 2 to about 6, provided that at least one of Z or R$^{11}$ in Formula IA is a COOR$^1$ group.

2. The method of claim 1 wherein the phosphorus-containing composition is characterized by Formula IA.

3. The method of claim 1 wherein the lubricant is characterized by Formula IA, Z is COOR$^1$, and R$^{11}$ is H or —COOR$^1$, and at least one of the R$^1$ groups is the same as R$^3$.

4. The method of claim 1 wherein the lubricant of Formula IA is further characterized by the formula $$RC(R^{10})(R^{11})—C(R^{10})(R)Z \qquad (II)$$

wherein R is independently $R^{10}$ or $(R^3O)_2P(O)$ provided that one R is $(R^3O)_2P(O)$ and the other is $R^{10}$, and $R^3$, $R^{10}$, $R^{11}$ and Z are as defined in claim 8.

5. The method of claim 1 wherein Z is —$COOR^1$, —$C(O)NR^4R^5$ or —$C(O)(OR^6)yN(R^4)C(O)R^7$.

6. A method for lubricating metal parts which comprises contacting said parts with a lubricant comprising at least one phosphorus-containing composition characterized by the formulae

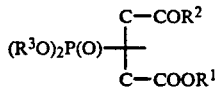

(IG)

wherein
- $R^1$ is a hydrocarbyl group or a hydrocarbyloxy hydrocarbyl group, and $R^1$ may be the same as $R^3$;
- $R^2$ is —$OR^1$, —$NR^4R^5$, —$(OR^6)yN(R^4)C(O)R^7$ or —$(OR^6)yOC(O)R^7$;
- $R^3$ is independently a hydrocarbyl group;
- $R^4$ and $R^5$ are each independently H or hydrocarbyl groups;
- $R^6$ is a hydrocarbylene group;
- $R^7$ is a hydrocarbyl group; and
- y is an integer from 1 to about 20.

7. The method of claim 6 wherein $R^2$ is $NR^4R^5$ where $R^4$ and $R^5$ are as defined in claim 1.

* * * * *